(12) United States Patent
Noshi et al.

(10) Patent No.: US 9,050,002 B2
(45) Date of Patent: Jun. 9, 2015

(54) IMAGE RECONSTRUCTING APPARATUS, X-RAY COMPUTED TOMOGRAPHY APPARATUS, AND IMAGE RECONSTRUCTING METHOD

(75) Inventors: Yasuhiro Noshi, Otawara (JP); Satoshi Saito, Yaita (JP)

(73) Assignees: KABUSHIKI KAISHA TOSHIBA, Tokyo (JP); Toshiba Medical Systems Corporation, Otawara-shi (JP)

( * ) Notice: Subject to any disclaimer, the term of this patent is extended or adjusted under 35 U.S.C. 154(b) by 950 days.

(21) Appl. No.: 12/861,319

(22) Filed: Aug. 23, 2010

(65) Prior Publication Data

US 2011/0052027 A1 Mar. 3, 2011

(30) Foreign Application Priority Data

Aug. 31, 2009 (JP) ................................. 2009-201009

(51) Int. Cl.
*G06K 9/00* (2006.01)
*A61B 6/03* (2006.01)
*G06T 11/00* (2006.01)
*A61B 6/00* (2006.01)

(52) U.S. Cl.
CPC ................. *A61B 6/032* (2013.01); *A61B 6/503* (2013.01); *A61B 6/541* (2013.01); *G06T 11/006* (2013.01); *G06T 2211/412* (2013.01)

(58) Field of Classification Search
None
See application file for complete search history.

(56) References Cited

U.S. PATENT DOCUMENTS

| | | | |
|---|---|---|---|
| 7,630,472 B2 | 12/2009 | Tsuyuki et al. | |
| 2005/0069081 A1* | 3/2005 | Kokubun et al. | 378/15 |
| 2009/0232379 A1* | 9/2009 | Kohler et al. | 382/131 |

FOREIGN PATENT DOCUMENTS

JP 2007-37782 2/2007

* cited by examiner

*Primary Examiner* — Neal Sereboff
(74) *Attorney, Agent, or Firm* — Oblon, McClelland, Maier & Neustadt, L.L.P.

(57) ABSTRACT

According to one embodiment, an apparatus includes a reconstructing unit, a first control unit, a detecting unit, a generating unit, and a second control unit. The first control unit controls the reconstructing unit to reconstruct first images based on projection data collected in first periods. The detecting unit detects second periods which belong to pulsation cycles different from one another and in which an organ to be imaged is in the substantially same form, based on the first images. The generating unit generates data for reconstruction including projection data for the required angle range by combining projection data collected in third periods close to the second periods. The second control unit controls the reconstructing unit to reconstruct a second image based the data for reconstruction.

19 Claims, 4 Drawing Sheets

IMAGE RECONSTRUCTING APPARATUS, X-RAY COMPUTED TOMOGRAPHY APPARATUS, AND IMAGE RECONSTRUCTING METHOD

CROSS-REFERENCE TO RELATED APPLICATIONS

This application is based upon and claims the benefit of priority from Japanese Patent Application No. 2009-201009, filed Aug. 31, 2009; the entire contents of which are incorporated herein by reference.

FIELD

Embodiments described herein relate generally to an image reconstructing apparatus, an X-ray computed tomography apparatus, and an image reconstructing method.

BACKGROUND

In an X-ray computed tomography apparatus (hereinafter referred to as the CT apparatus) having a narrow cone angle, projection data regarding the total of the heart cannot be sufficiently collected by scanning it as much as one rotation of an X-ray tube. To solve the above problem, helical scan is carried out at a slow helical pitch. Thus, in a CT apparatus having a wide cone angle, there is a case where the projection data regarding the total of the heart can be collected by the scan of one rotation of the X-ray tube. In this case, the projection data can be collected by volume scan without any movement of a bed.

Now, in examination of the heart in which the CT apparatus is used, it is one of important themes to improve a temporal resolution of an image. As a major method of dealing with this theme, there is a so called half EGR method in which both of a half reconstruction method and an electrocardiograph-gated reconstruction (EGR) method are used. As is well known, in this method, there is cut out a half projection data set which is collected during a time period for rotating an X-ray tube in an angle range of 180°+ a fan angle round a heartbeat phase designated by an operator. Further, an image is reconstructed from the half projection data set. The above heartbeat phase means that a time period from an R wave to the next R wave is standardized in a range of 0 to 100%, and a time point in the time period is expressed with a value of percentage.

According to the above method, the improvement of the temporal resolution can be achieved in contrast to a case of the scan over 360°. However, a time required for rotating the X-ray tube in an angle range of 180°+ the fan angle is restricted as a temporal resolution. Therefore, it is inevitable to deteriorate an image quality by blur or the like due to a change in a mode of the heart with the heartbeat which is brought about during a time period required for rotating the X-ray tube in an angle range of 180°+ the fan angle.

A segment EGR method is known as an image reconstructing method having the higher temporal resolution than in the case of the half EGR method. In the segment EGR method, projection data acquired in respective projection directions within an angle range of 180°+ the fan angle and at a timing near to a specific heartbeat phase are selected from a number of projection data collected during time periods corresponding to plural heartbeats, thereby obtaining the half projection data set. That is, the half projection data set is obtained by collecting the projection data acquired in substantially the same heartbeat phase from the projection data collected at respective different heartbeat periods. Consequently, time differences among timings for acquiring the respective projection data included in the half projection data set are increased, but time shifts based on a specific heartbeat phase are reduced, and hence the substantial temporal resolution is improved.

It is to be noted that a document that discloses a relevant technique is Jpn. Pat. Appin. KOKAI Publication No. 2007-037782.

However, the moving state of the heart may considerably vary, and there is no guarantee that the forms of the heart in the same heartbeat phase under the above definition are the same at two different points of time.

Therefore, in the segment EGR method, when there is no reproducibility of the motion of the heart during a plurality of heartbeat cycles in which a plurality of pieces of projection data included in a half projection data set are acquired, there is a fear that blurring occurs in a reconstructed image.

In particular, in the case of volume scan, it is difficult to smoothly mutually couple the projection data of a plurality of heartbeat cycles because of no movement of a bed, and hence the blurring in a reconstructed image is more remarkable than in the case of the helical scan.

Under such circumstances, it has been demanded to reconstruct an image with the high temporal resolution and the less blurring by the segment EGR method.

DETAILED DESCRIPTION

In general, according to one embodiment, an image reconstructing apparatus includes reconstructing unit, first control unit, detecting unit; generating unit, and second control unit. The reconstructing unit reconstructs an image of a imaging region including an organ to be imaged that pulsates in a subject based on a portion of projection data collected by a scanner that collects projection data of the subject in each of a number of projection directions by use of X-rays during a collection period including at least two pulsation cycles of the organ to be imaged. The first control unit controls the reconstructing unit to reconstruct a plurality of first images based on projection data collected in a plurality of first periods in the collection period of the projection data. The detecting unit detects a plurality of second periods which belong to pulsation cycles different from one another and in which the organ to be imaged is in the substantially same form, based on the plurality of first images. The generating unit generates data for reconstruction including projection data for the required angle range by combining projection data collected in a plurality of third periods close to the plurality of second periods detected by the detecting unit of the projection data. The second control unit controls the reconstructing unit to reconstruct a second image based on projection data included in data for reconstruction generated by the generating unit.

Hereinafter, embodiments will be explained with reference to the drawings.

Figure 1:
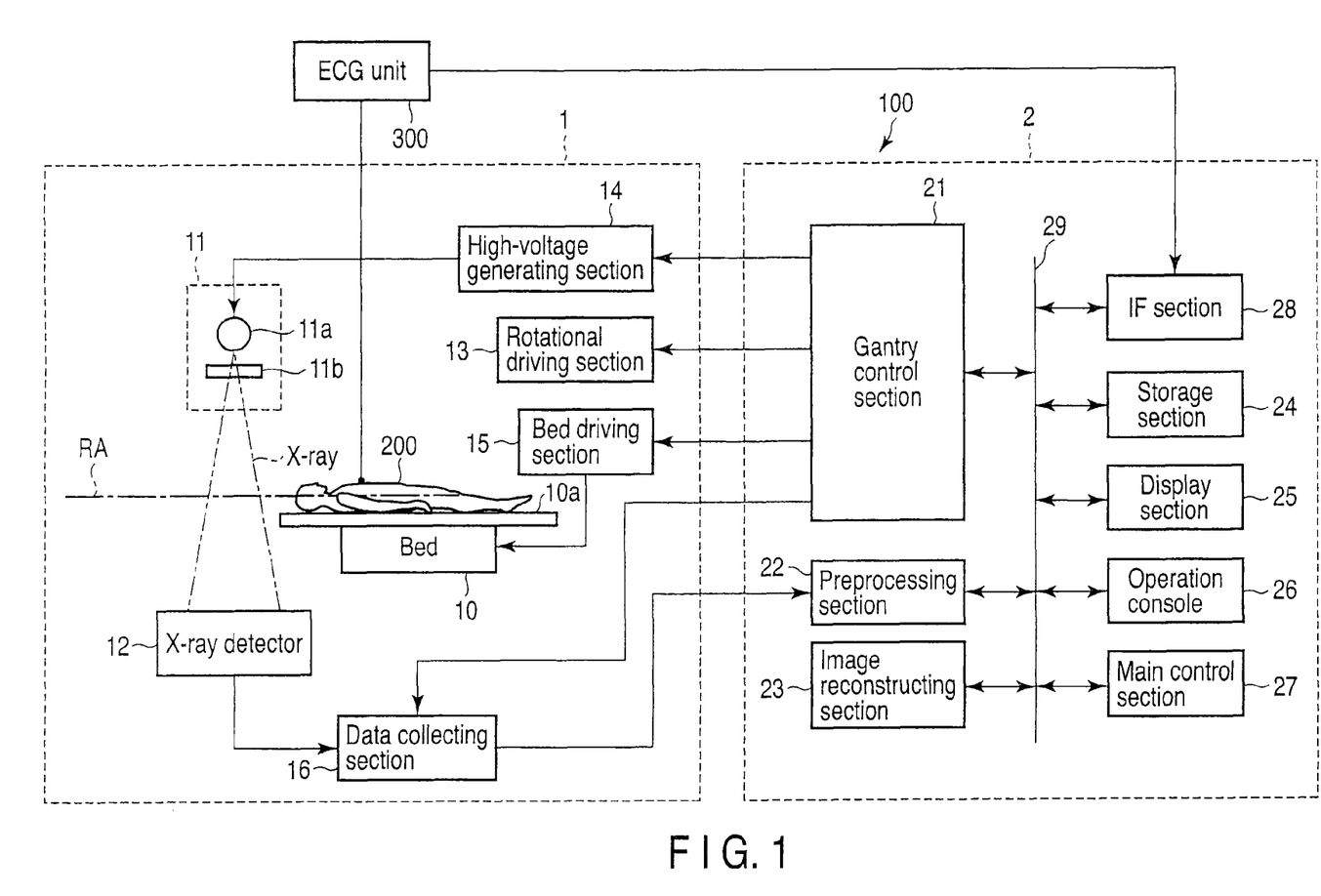
FIG. 1 is a diagram showing a configuration of the main portion of an X-ray computed tomography apparatus according to an embodiment.

FIG. 1 is a diagram showing a configuration of the main portion of a CT apparatus 100 according to the present embodiment. The CT apparatus 100 includes a scan gantry 1 and a computer device 2. The scan gantry 1 is a constitutional component to collect projection data of a subject 200. The projection data collected by the scan gantry 1 is subjected to processing of image reconstruction and others by the computer device 2.

The scan gantry 1 includes a bed 10, an X-ray tube device 11, an X-ray detector 12, a rotational driving section 13, a high-voltage generating section 14, a bed driving section 15, and a data collecting section 16.

The X-ray tube device 11 and the X-ray detector 12 are mounted in opposition to an annular rotational rack which is not shown. The rotational rack is driven and rotated by the rotational driving section 13. At this time, the X-ray tube device 11 and the X-ray detector 12 rotate round a rotation axis RA. The scan gantry 1 forms a hollow (imaging space) inside the rotation orbit of the X-ray tube device 11 and the X-ray detector 12. That is, the CT apparatus 100 is of a so called rotate/rotate type. However, the embodiment can be carried out similarly by any of various other known types such as a stationary/rotate type.

The X-ray tube device 11 includes an X-ray tube 11a and an X-ray filter 11b. The X-ray tube 11a receives power supply from the high-voltage generating section 14 to radiate X-rays toward the X-ray detector 12. The X-ray filter 11b removes lower energy components of the X-rays radiated from the X-ray tube 11a to reduce exposure. The high-voltage generating section 14 comprises a high-voltage transformer, a filament current generator, and a rectifier. In addition thereto, the high-voltage generating section 14 includes a tube voltage switching device and a filament current switching device to adjust a tube voltage and a filament current arbitrarily or stepwise. It is to be noted that the X-ray tube device 11 has a function to radiate X-rays as so called cone beams in the shape of a cone (a circular cone or a pyramid).

The X-ray detector 12 has a plurality of element strings including a plurality of X-ray detecting elements, respectively. The plurality of element strings are arranged in a direction along the rotation axis RA. Each of the plurality of X-ray detecting elements outputs an electric signal in accordance with the intensity of the incident X-ray.

The subject 200 is mounted on a top plate 10a of the bed 10. The bed 10 is driven by the bed driving section 15, and the top plate 10a is moved in a lengthwise direction thereof (in a horizontal direction in FIG. 1). Usually, the bed 10 is installed so that the lengthwise direction is in parallel with the rotation axis RA. Further, the subject 200 is usually mounted on the top plate 10a so that the axis of a body is along the rotation axis RA. Thus, the subject 200 is inserted into the hollow of the scan gantry 1 as the top plate 10a moves.

The data collecting section 16 collects the output of the X-ray detector 12 as scan data and supplies the data to the computer device 2. Between the X-ray detector 12 and the data collecting section 16, an interface using a slip ring, optical communication or the like is interposed. In consequence, the data collecting section 16 can collect the output of the X-ray detector 12 while continuously rotating the rotational rack.

The computer device 2 comprises a gantry control section 21, a preprocessing section 22, an image reconstructing section 23, a storage section 24, a display section 25, an operation console 26, a main control section 27, and an interface section (IF section) 28. The gantry control section 21, the preprocessing section 22, the image reconstructing section 23, the storage section 24, the display section 25, the operation console 26, the main control section 27, and the interface section 28 are connected to one another via a data/control bus 29.

The gantry control section 21 controls the operation of the scan gantry 1 so that scan to obtain scan data necessary for a diagnose is performed.

The preprocessing section 22 performs preprocessing such as sensitivity correction for the scan data supplied from the data collecting section 16. The scan data after being subjected to the preprocessing by the preprocessing section 22 is stored in the storage section 24 as the projection data.

The image reconstructing section 23 reconstructs a tomographic image of the subject 200 based on the projection data stored in the storage section 24. In the image reconstructing section 23, the image reconstruction can be carried out by appropriately using any of various well-known reconstructing methods, but each of the usable reconstructing methods includes at least a process to reconstruct an image from a half projection data set. The image reconstructing section 23 outputs image data representing a reconstructed tomographic image.

The storage section 24 temporarily stores the projection data and image data. As the storage section 24, for example, a hard disk drive (HDD) or a random access memory (RAM) can be utilized.

The display section 25 displays a tomographic image based on the image data stored in the storage section 24.

The operation console 26 is provided so that an operator can input, for example, various pieces of information such as imaging conditions and various instructions. The operation console 26 comprises an operation screen.

The main control section 27 comprises a function to totally control the operations of the respective portions of the CT apparatus 100 to perform the various operations realized by an already existing CT apparatus. The main control section 27 additionally comprises various functions as follows. The main control section 27 is realized by, for example, a combination of a processor and a memory. Thus, the various functions are realized by executing programs stored in the memory with the aid of the processor.

One of the functions is to control the image reconstructing section 23 to reconstruct a number of comparative images as a number of first images based on the half projection data set collected respectively in a number of first periods shifted from one another with respect to time. One of the functions is to extract a region corresponding to the heart as an organ to be imaged from the number of comparative images. One of the functions is to detect a low-speed fluctuation period as a plurality of second periods which belong to heartbeat cycles different from one another and in which the magnitude as the feature quantity of the region of the heart is substantially the same, based on the first images. One of the functions is to generate a half projection data set by combining projection data collected in a plurality of third periods respectively close to a plurality of pulsation phases included in the plurality of detected low-speed fluctuation periods. One of the functions is to control the image reconstructing section 23 so as to reconstruct a diagnostic image as a second image based on the projection data included in the half projection data set generated as described above.

To the interface section 28, an external device, such as an ECG unit 300, is connected appropriately. The interface section 28 interfaces the delivery of information between an external device connected and the computer device 2. The ECG unit 300 detects an ECG signal as a biological signal of the subject 200 and supplies the ECG signal to the computer device 2 after adjusting the ECG signal into a state of being easily handled by the computer device 2.

Next, the operation of the CT apparatus 100 configured as described above will be explained.

It is possible for the CT apparatus 100 to perform various imaging realized by the already existing CT apparatus but no explanation of this is given. Here, imaging operations peculiar to the CT apparatus 100 which is not realized by the already existing CT apparatus will be explained.

Figure 2:
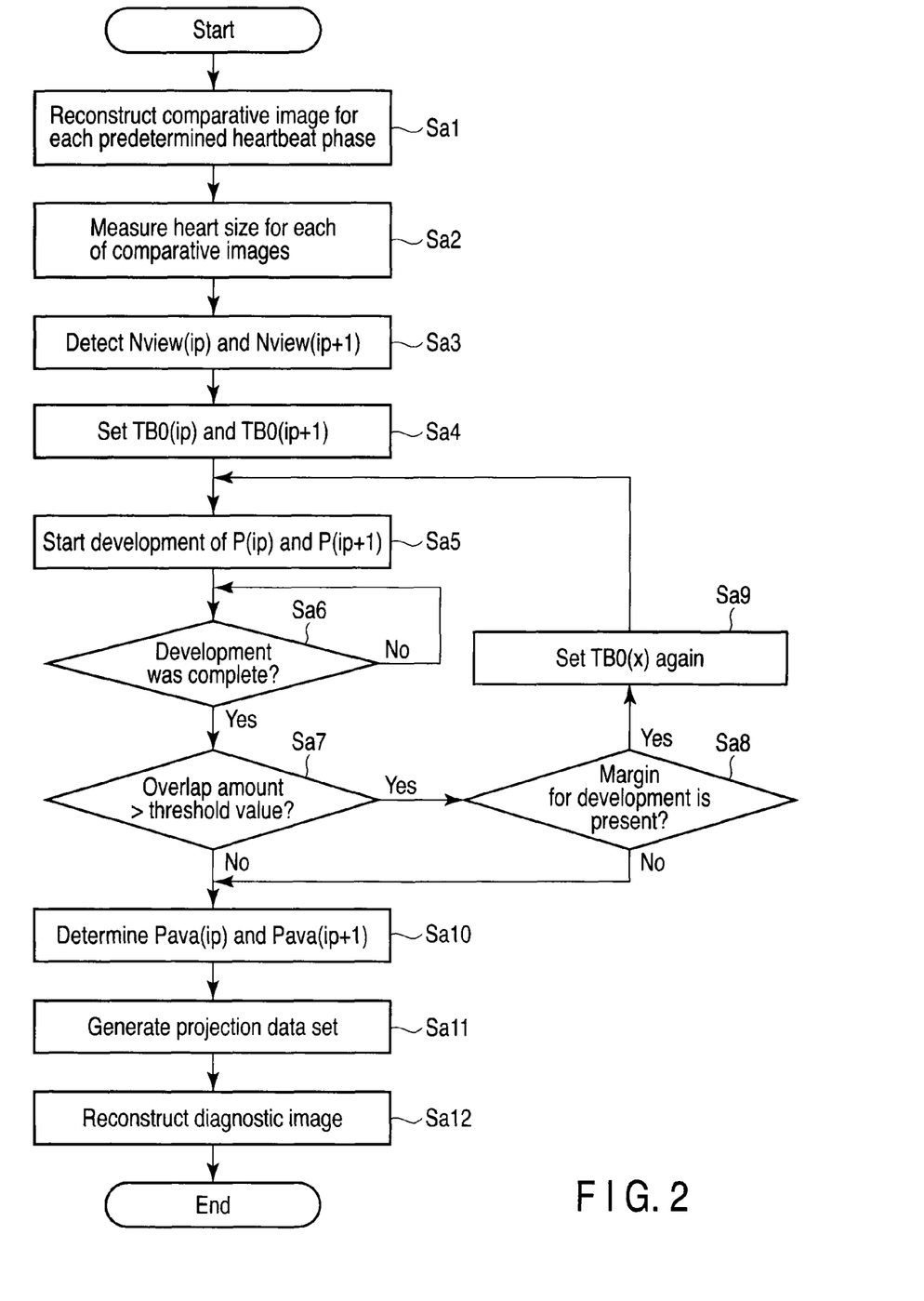
FIG. 2 is a flowchart showing a processing procedure of a main control section in FIG. 1 during image reconstruction by a segment EGR method.

FIG. 2 is a flowchart showing a processing procedure of the main control section 27 when reconstructing an image by the segment EGR method.

The main control section 27 instructs the gantry control section 21 to perform volume scan of the region including the heart of the subject 200 during a plurality of heartbeat cycles before initiating the processing shown in FIG. 2. The scan gantry 1 performs the operation to collect projection data under the control of the gantry control section 21 in response to the instruction. Then, the scan data collected by the data collecting section 16 is processed into projection data by the preprocessing section 22 and then stored in the storage section 24. At this time, managerial information to identify which projection direction each piece of projection data is acquired and which heartbeat phase in which heartbeat cycle each piece of projection data is obtained is also stored in the storage section 24. In the CT apparatus 100, one heartbeat cycle is defined as a period from an R wave of the ECG signal output from the ECG unit 300 to the next R wave. Then, the heartbeat cycle is normalized into a range of 0 to 100% and the heartbeat phase is defined as that which is represented by percentage at the point of time in the period. However, the reference of the heartbeat cycle may be determined by a timing other than the R wave. Further, the heartbeat phase may be represented as an elapsed time after the reference timing, such as the R wave.

When volume scan is performed during three or more heartbeat cycles, it is also possible to reconstruct a diagnostic tomographic image (diagnostic image) based on the half projection data including projection data selected from the projection data collected in the three or more heartbeat cycles, respectively, or to reconstruct a plurality of diagnostic images. However, here, only the projection data collected in two heartbeat cycles, that is, an ip-th heartbeat cycle B(ip) and a (ip+1)-th heartbeat cycle B(ip+1), respectively, is focused on and the operation to reconstruct only one diagnostic image will be explained.

In step Sa1, the main control section 27 controls the image reconstructing section 23 to reconstruct a comparative image regarding the axial surface based on the projection data collected in the first period around the heartbeat phase for each predetermined heartbeat phase in the heartbeat cycles B(ip) and B(ip+1). For the reconstruction of a comparative image, for example, a general half reconstruction method is used. When the half reconstruction method is used, the first period is a period required to collect projection data in an angle range of 180°+ a fan angle. It is arbitrary to reconstruct a comparative image in which heartbeat cycle and, for example, a comparative image is reconstructed for each 1% heartbeat cycle. In this case, 100 comparative images are reconstructed for one heartbeat cycle. These comparative images are stored in the storage section 24. It is assumed that these comparative images are relative to one and the same axial surface. Then, it is possible to determine the position of the axial surface fixedly in the CT apparatus 100 or arbitrarily change the position in the range of volume scan in accordance with the instruction by a user. When the position of the axial surface is determined fixedly, the position is typically determined in the center of the range of volume scan, but this is not limited.

In step Sa2, the main control section 27 measures the magnitude as the feature quantity of the heart region in each comparative image with respect to each of the plurality of comparative images reconstructed in step Sa1. Specifically, this can be realized by binarizing the axial image by an appropriate threshold value that distinguishes the air region from other regions and then by measuring the magnitude (area) of the regions other than the air region.

In step Sa3, the main control section 27 detects low-speed fluctuation periods Nview(ip) and Nview(ip+1), respectively, with respect to the heartbeat cycles B(ip) and B(ip+1). The slow-speed fluctuation period is a period during which the change in the size of the heart is small. It may be possible to detect the slow-speed fluctuation period as, for example, a period during which a variation of size with respect to time (differential value) measured in step Sa2 is less than or equal to a certain level.

Figure 3:
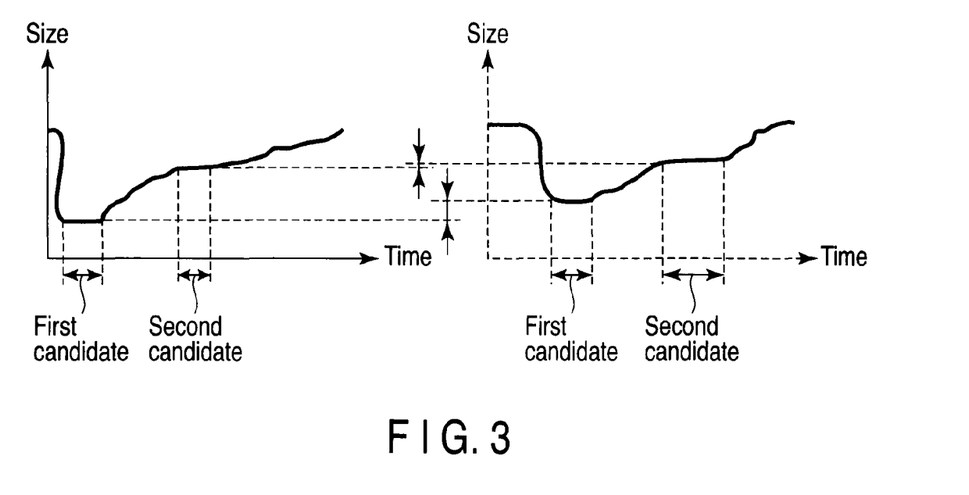
FIG. 3 is a diagram showing an example of a change in the size of a heart region with time.

FIG. 3 is a diagram showing an example of a change in the size of a heart region with time in the heartbeat cycles B(ip) and B(ip+1). In FIG. 3, the graph on the left side relates to the heartbeat cycle B(ip) and the graph on the right side to the heartbeat cycle B(ip+1).

In general, it is known that the motion of the heart is small at the end of the systolic period and in the middle of the diastolic period in one heartbeat cycle. Because of this, candidates of the slow-speed fluctuation period are detected at the end of the systolic period and in the middle of the diastolic period as a result (a first candidate and a second candidate in FIG. 3). As shown in FIG. 3, even if there is a large difference in the way of the change in the size of the heart with time between the heartbeat cycles B(ip) and B(ip+1), it is possible to easily distinguish between the end of the systolic period and the middle of the diastolic period in each heartbeat cycle from the trend of change. Therefore, it is recommended to receive a user's instruction as to which period the user desires between the end of the systolic period and the middle of the diastolic period in advance or at this point of time and employ the candidate of the low-speed fluctuation period closer to that desired by the user as the low-speed fluctuation period. However, there is a case where it is not possible to recognize the end of the systolic period or the end of the diastolic period due to arrhythmia etc, and therefore, it is not necessarily required to receive a user's instruction. Here, it is assumed that the second candidate is detected as the slow-speed fluctuation periods Nview(ip) and Nview(ip+1) for both the heartbeat cycles B(ip) and B(ip+1). It may also be possible to compare the typical value (minimum value, maximum value, average value, etc.) of the size of the heart between each candidate of the slow-speed fluctuation period in the heartbeat cycle B(ip) and each candidate of the slow-speed fluctuation period in the heartbeat cycle B(ip+1) and detect the candidates included in a combination with which the difference is minimum as the slow-speed fluctuation periods Nview (ip) and Nview(ip+1).

In step Sa4, the main control section 27 sets tube positions TB0(ip) and TB0(ip+1) with respect to the heartbeat cycles B(ip) and B(ip+1), respectively. Specifically, the main control section 27 determines gating points GP(ip) and GP(ip+1) with respect to the heartbeat cycles B(ip) and B(ip+1) as the center phases of the slow-speed fluctuation periods Nview(ip) and Nview(ip+1), respectively. Then, the main control section 27 sets the projection directions in the gating points GP(ip) and GP(ip+1) as the tube points TB0(ip) and TB0(ip+1), respectively.

Figure 5:
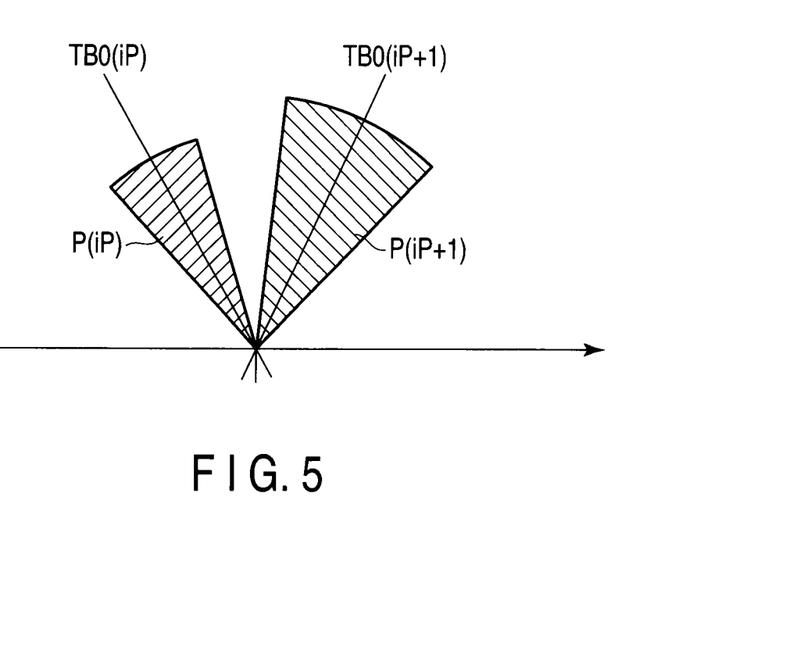
FIG. 5 is a diagram showing a setting example of a tube position.

FIG. 5 is a diagram showing an example of the settings of the tube positions TB0(ip) and TB0(ip+1).

Figure 4:
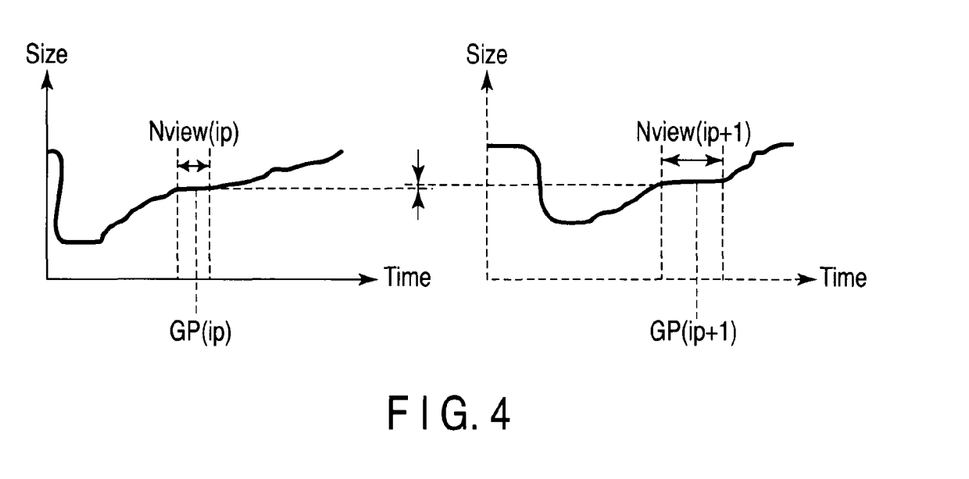
FIG. 4 is a diagram showing a setting example of a gating point.
Figure 6:
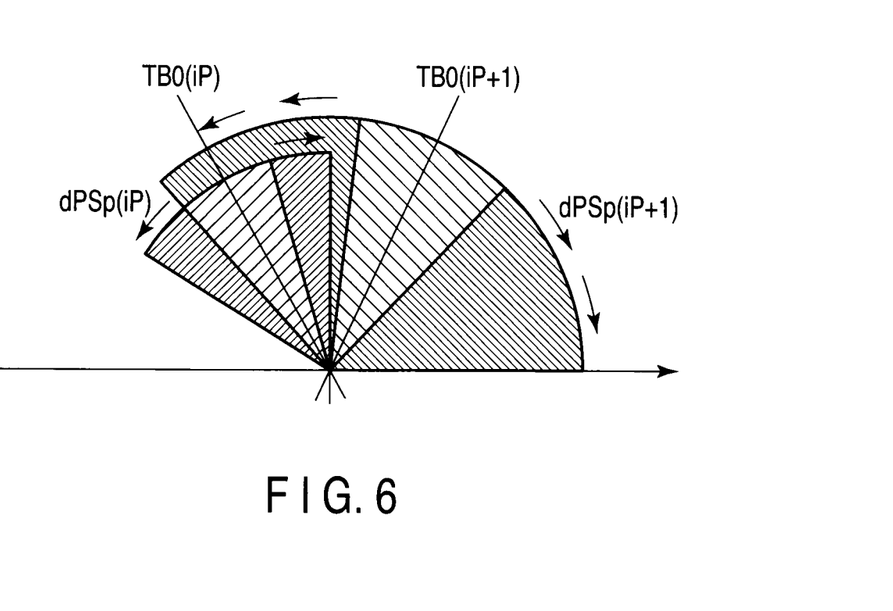
FIG. 6 is a diagram showing an example of a difference between development speeds of two heartbeat cycles.

In step Sa5, the main control section 27 starts the development of patches P(ip) and P(ip+1) with respect to the heartbeat cycles B(ip) and B(ip+1), respectively. Here, the patches P(ip) and P(ip+1) denote angle ranges around the tube positions TB0 (ip) and TB0 (ip+1), respectively, as shown in FIG. 5. Then, the development of the patch is to widen of the patch at a fixed speed (hereinafter, referred to as a development speed). The development speed of the patches P(ip) and P(ip+1), respectively, may be the same and set to a fixed value, but here, development speeds dPSp(ip) and dPSp(ip+1) of the patches P(ip) and P(ip+1) are determined, respectively, in accordance with the sizes of the slow-speed fluctuation periods Nview(ip) and Nview(ip+1). As shown in FIG. 4, when a relationship of Nview(ip)<Nview(ip+1) holds, then the development speeds dPSp(ip) and dPSp(ip+1) are determined so that a relationship of dPSp(ip)<dPSp(ip+1) holds, as shown in FIG. 6. When the development speed of the heartbeat cycle in which the slow-speed fluctuation period is long is set greater than the development speed of the heartbeat period in which the slow-speed fluctuation period is short, a relationship between the length of the slow-speed fluctuation period and the development speed may be arbitrary and it is only required to set them in accordance with the rules determined in advance to fulfill the conditions.

In step Sa6, the main control section 27 waits for the completion of the development of the patches P(ip) and P(ip+1). Then, when the patches P(ip) and P(ip+1) are developed so that a continuous angle range of 180°+ a fan angle is covered by a combination of a partial region of the patch P(ip) and a partial region of the patch P(ip+1), the main control section determines that the development of the patches is completed. In this case, the main control section 27 advances the procedure from step Sa6 to step Sa7.

In step Sa7, the main control section 27 checks whether or not an overlap amount of the patches P(ip) and P(ip+1) is greater than a threshold value th_OverLapView. This check is realized by, for example, checking whether or not the following conditional expression holds where a continuation time of the development of the patches P(ip) and P(ip+1) is represented by t.

$$\{TB(ip+1)+dPSp(ip+1)\times t\}-\{TB(ip)+dPSp(ip+1)\times t\}>th\_OverLapView$$

Then, when the overlap amount is greater than the threshold value th_OverLapView, the main control section 27 advances the procedure from step Sa1 to step Sa8.

In step Sa8, the main control section 27 checks whether or not there is margin for development of the patch relative to the slow-speed fluctuation period Nview(ip) or Nview(ip+1) which is longer (hereinafter, referred to as a patch P(x)). This check is realized by, for example, checking whether or not the following conditional expression holds. Here, that of the development speeds dPSp(ip) and dPSp(ip+1) which relates to the patch P(x) is represented as dPSp(x) and that of the slow-speed fluctuation periods Nview(ip) and Nview(ip+1) which is longer is represented as Nview(x).

$$dPSp(x)\times t<Nview(x)/2$$

When there is margin for development of the patch P(x), the main control section 27 advances the procedure from step Sa8 to step Sa9.

In step Sa9, the main control section 27 sets the tube position TB0(x) again. Here, the tube position TB0(x) is that which relates to the patch P(x) of the tube positions TB0(ip) and TB0(ip+1). Then, the setting of the TB0(x) for the second time is realized by, for example, calculating the following expression. Here, the number of projection directions per revolution of the X-ray tube 11a is represented as ViewRev.

$$TB0(x)=TB0(x)-\{Nview(x)/2-dPSp(x)\times t\}\times 360/ViewRev$$

As described above, when Nview(ip) is greater than Nview (ip+1), the tube position TB0(ip) is set again and when Nview (ip+1) is greater than Nview(ip), the tube position TB0(ip+1) is set again, respectively. When the Nview(ip) and Nview(ip+1) are the same in magnitude, then, it is only required to set that which is determined in advance of the TB0(ip) and TB0 (ip+1) again. After either of the TB0(ip) and TB0(ip+1) is set again, the main control section 27 performs processing after step Sa5 again relative to the tube position set again and the other tube position that is set in step Sa4 and remains as it is.

When the overlap amount is less than or equal to the threshold value th_OverLapView, the main control section advances the procedure from step Sa1 to step Sa10. When there is no margin for development of the patch P(x), the main control section 27 advances the procedure from step Sa8 to step Sa10.

In step Sa10, the main control section 27 determines available patch regions Pava(ip) and Pava(ip+1), respectively, with respect to the patches P(ip) and P(ip+1). The available patch regions Pava(ip) and Pava(ip+1) are determined as angle regions that belong to the patch P(ip) and P(ip+1), respectively, and at the same time, which cover a continuous angle range of 180°+ a fan angle by combination and which do not overlap each other. The available patch regions Pava(ip) and Pava(ip+1) may be selected arbitrarily from the patches P(ip) and P(ip+1), respectively, and it is only required to determine the available patch regions Pava(ip) and Pava(ip+1), respectively, in accordance with the rules determined in advance to fulfill the conditions. However, it is desirable to make available the patch which is longer of the slow-speed fluctuation periods Nview(ip) and Nview(ip+1) as to the region where the patches P(ip) and P(ip+1) overlap each other.

In step Sa11, the main control section 27 selects the projection data acquired respectively in the heartbeat phase closest to the gate point GP(ip) in each projection direction included in the available patch region Pava(ip) and the projection data acquired respectively in the heartbeat phase closest to the gating point GP(ip) in each projection direction included in the available patch region Pava(ip+1) from the storage section 24 and generates a half projection data set as a set of the projection data.

In step Sa12, the main control section 27 instructs the image reconstructing section 23 to reconstruct a diagnostic image by the half projection method based on the half projection data set generated as described above.

As described above, according to the CT apparatus 100, reconstruction of a diagnostic image is performed based on the half projection data set generated by combining only the projection data acquired in the vicinity of the slow-speed fluctuation periods Nview(ip) and Nview(ip+1) in which the change in the size of the heart in the respective heartbeat cycles B(ip) and B(ip+1) is small and at the same time, the difference in size of the heart between the respective cycles is small, and therefore, although the reconstruction is performed by mixing a plurality of pieces of the heartbeat data by the segment EGR method, it is possible to obtain a reconstructed image of high quality in which blurring is suppressed.

Further, according to the CT apparatus 100, the size of the heart in each heartbeat phase is measured as the size of the heart region extracted as the regions other than the air region of the axial image for each heartbeat phase, and therefore, it is possible to accurately grasp the size of the heart in each heartbeat phase by reducing the influence of the movement of other organs, such as a lung, and to appropriately detect the low-speed fluctuation periods Nview(ip) and Nview(ip+1).

According to the CT apparatus 100, when the patch P(ip) and the patch P(ip+1) overlap considerably, the difference in angle between the tube position TB0(ip) and the tube position TB0(ip+1) is increased and then the patches P(ip) and P(ip+1) are developed again, and therefore, it is possible to reduce the overlap amount of the patches, that is, to reduce the resonance of the development of the patch P(ip) and the development of the patch P(ip+1). In consequence, it is possible to satisfactorily select the available patch regions Pava(ip) and Pava(ip+1), respectively, from both the patches P(ip) and P(ip+1) and to improve the temporal resolution efficiently. Further, according to the CT apparatus 100, the tube position which is longer of the low-speed fluctuation periods Nview(ip) and Nview(ip+1) is set again in order to increase the difference in angle between the tube position TB0(ip) and the tube position TB(ip+1), and therefore, it is possible to include and keep both the tube positions TB(ip) and TB(ip+1) after being set again in the low-speed fluctuation periods Nview(ip) and Nview(ip+1), respectively. Because of this, it is possible to regard most of the projection data included in the half projection data set as that acquired during the low-speed fluctuation periods Nview(ip) and Nview(ip+1).

According to the CT apparatus 100, the development speed of the patch which is longer of the low-speed fluctuation periods Nview(ip) and Nview(ip+1) is set greater than the development speed of the other patch, and therefore, it is possible to suppress the possibility that the period corresponding to each patch protrudes from the low-speed fluctuation period or to reduce the amount of protrusion when it protrudes. As a result, it is possible to regard most of the projection data included in the half projection data set as that acquired during the low-speed fluctuation periods Nview(ip) and Nview(ip+1).

The present embodiment can be modified in a variety of ways as follows.

The heartbeat phase may be detected based on the change in the size of the heart. In this case, the use of the ECG unit 300 may be obviated.

Organs to be imaged may be any one as long as it pulsates, such as a lung, in addition to the heart.

It is also possible to perform the processing in the embodiment in an image reconstructing apparatus that reconstructs a diagnostic image based on the projection data collected by a separate X-ray scanner.

Any feature quantity may be used as long as it can change in accordance with a change in the form of a region corresponding to an organ to be imaged. For example, it is also possible to use the width in a specified position (for example, the center position) in a comparative image of the region or the length of the contour of the region as a feature quantity. It is also possible to reconstruct respective comparative images as to a plurality of axial surfaces with respect to one heartbeat phase, to find the volume of the region corresponding to an organ to be imaged based on the plurality of comparative images, and then to use the volume as a feature quantity.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An imaging apparatus comprising:
    a scanner that collects projection data of an organ pulsating in a subject in each of a number of projection directions by use of X-rays during a collection period including at least two pulsation periods of the organ to be imaged;
    a computer configured to execute program instructions to produce an object image of the organ based on the collected projection data; and
    a memory storing program instructions which when executed by said computer results in generation of the object image by the computer performing the following steps,
        reconstructing an image of a imaging region including the organ to be imaged based on a portion of the projection data,
        first controlling the reconstructing to reconstruct a plurality of first images relative to a same axial surface based on projection data collected in a plurality of first periods in the collection period of the projection data,
        detecting a plurality of second periods which belong to respective different pulsation periods different from one another and in which the organ to be imaged is in the substantially same form, based on the plurality of first images,
        generating data for reconstruction including projection data for a required angle range by combining projection data collected in a plurality of third periods close to the plurality of second periods detected by the detecting of the projection data, and
        second controlling the reconstructing to reconstruct a second image based on projection data included in data for reconstruction generated by the generating, said second image being said object image.

2. The image reconstructing apparatus according to claim 1, further comprising;
    said memory storing a program instruction defining a step of measuring feature quantities of regions corresponding to the organ to be imaged from the plurality of first images, wherein
    the detecting detects the plurality of second periods by the comparison of the feature quantities.

3. The imaging apparatus according to claim 1, wherein in regard to the program instructions stored in said memory and the detecting step executed by the computer, each second period is only a part of the pulsation period to which it belongs.

4. The image reconstructing apparatus according to claim 2, wherein
    the detecting detects, for each of the plurality of pulsation cycles, a low-speed fluctuation period during which a state where a variation of the feature quantities per unit time is smaller than a specified variation continues beyond a specified period, selects a plurality of pulsation phases which belong to pulsation cycles different from one another and in which the feature quantities are substantially the same from among the pulsation phases included in the plurality of detected low-speed fluctuation periods, and detects the plurality of third periods as a plurality of periods different from one another including the plurality of selected pulsation phases.

5. The image reconstructing apparatus according to claim 4, wherein
the generating step includes:
selecting one of the projection directions regarding the projection data collected by the scanner in the low-speed fluctuation period detected by the detecting unit, for each of the plurality of pulsation cycles;
setting an angle range of a specified angle around the projection direction selected, for each of the plurality of pulsation cycles;
widening the angle ranges set for the plurality of pulsation cycles until the required angle range is obtained by combining at least portions of the angle ranges of the plurality of pulsation cycles;
selecting at least partial ranges that cover the whole of the required angle range by combining the plurality of widened angle ranges, and that do not overlap one another for the plurality of pulsation cycles; and uses the selected at least partial ranges as available angle ranges
extracting projection data collected in the second periods from the projection data collected by the scanner, the second periods being the collection period of projection data in the projection direction in the available angle range selected for the same pulsation period in the slow-speed fluctuation period detected by the detecting for each of the plurality of pulsation cycles or at a timing closest to the low-speed fluctuation period; and
generating the data for reconstruction as data including all of the extracted projection data.

6. The image reconstructing apparatus according to claim 5, wherein
when an overlap amount of two of the plurality of widened angle ranges is greater than a specified overlap amount, the generating step selects the projection direction again to increase an angle between the two projection directions selected as a center of the two angle ranges, and then carries out the setting of the angle ranges and the widening of the angle ranges again, respectively.

7. The image reconstructing apparatus according to claim 5, wherein
the generating step increases a widening speed of the angle range all the more, as the low-speed fluctuation period detected by the detecting step for the pulsation cycle having the set angle range is longer.

8. An X-ray computed tomography apparatus comprising:
a scanner configured to collect projection data of an organ pulsating in a subject for each of a number of projection directions using X-rays;
computer circuitry configured:
to control the scanner to collect the projection data of a imaging region including the organ to be imaged that pulsates in the subject during a collection period including at least two of pulsation cycles of the organ to be imaged,
to reconstruct an image of the imaging region based on a portion of the projection data collected by the scanner,
to control the reconstructing to reconstruct a plurality of first images relative to a same axial surface based on each piece of projection data collected in a plurality of first periods in the collection period of the projection data;
to detect a plurality of second periods which belong to respective different pulsation periods different from one another and in which the organ to be imaged is in the substantially same form, based on the plurality of first images, wherein each second period is only a part of the pulsation period to which it belongs,
to generate data for reconstruction including projection data for a required angle range by combining projection data collected in each of a plurality of third periods respectively close to the plurality of second periods detected by the detecting of the projection data, and
to control the reconstructing to reconstruct a second image, which is an image of the organ, based on projection data included in the generated data for reconstruction.

9. The X-ray computed tomography apparatus according to claim 7, wherein the computer circuitry is further configured to measure feature quantities of regions corresponding to the organ to the computer circuitry is further be imaged from the plurality of first images, and
to detect the plurality of second periods by the comparison of the feature quantities.

10. The X-ray computed tomography apparatus according to claim 9, wherein
the computer circuitry is further configured, for each of the plurality of pulsation cycles, to detect a low-speed fluctuation period during which a state where a variation of the feature quantities per unit time is smaller than a specified variation continues beyond a specified period, select a plurality of pulsation phases which belong to pulsation cycles different from one another and in which the feature quantities are substantially the same from among the pulsation phases included in the plurality of detected low-speed fluctuation periods, and detect the plurality of third periods as a plurality of periods different from one another including the plurality of selected pulsation phases.

11. The X-ray computed tomography apparatus according to claim 10, wherein
the computer circuitry is further configured:
to select one of the projection directions regarding the projection data collected by the scanner in the low-speed fluctuation period detected by the detecting unit, for each of the plurality of pulsation cycles;
to set sets an angle range of a specified angle around the projection direction selected, for each of the plurality of pulsation cycles;
to widen the angle ranges set for the plurality of pulsation cycles until the required angle range is obtained by combining at least portions of the angle ranges of the plurality of pulsation cycles;
to select at least partial ranges that cover the whole of the required angle range by combining the plurality of widened angle ranges, and that do not overlap one another for the plurality of pulsation cycles; and uses the selected at least partial ranges as available angle ranges;
to extract projection data collected in the second periods from the projection data collected by the scanner, the second periods being the collection period of projection data in the projection direction in the available angle range selected for the same pulsation period in the slow-speed fluctuation period detected by the detecting for each of the plurality of pulsation cycles or at a timing closest to the low-speed fluctuation period; and
to generate the data for reconstruction as data including all of the extracted projection data.

12. The X-ray computed tomography apparatus according to claim 11, wherein when an overlap amount of two of the plurality of widened angle ranges is greater than a specified overlap amount, the computer circuitry is configured to select the projection direction again to increase an angle between the two projection directions selected as a center of the two angle ranges, and then carries out the setting of the angle ranges and the widening of the angle ranges again, respectively.

13. The X-ray computed tomography apparatus according to claim 11, wherein
the computer circuitry is configured to increase a widening speed of the angle of the angle range all the more, as the low-speed fluctuation period detected by the detecting for the pulsation cycle having the set angle range is longer.

14. An imaging method comprising:
transmitting X-rays, using an X-ray scanner, through an organ to be imaged, said organ pulsating in a subject;
collecting projection data of the organ in each of a number of projection directions by use of the X-rays during a collection period including at least two of pulsation cycles;
reconstructing, using a computer, a plurality of first images relative to a same axial surface based on each piece of projection data collected in a plurality of first periods in a collection period of the projection data of a imaging region including the organ to be imaged;
detecting, using the computer, a plurality of second periods which belong to respective different pulsation periods different from one another and in which the organ to be imaged is in the substantially same form, based on the plurality of first images, wherein each second period is only a part of the pulsation period to which it belongs;
generating, using the computer, data for reconstruction including projection data for a required angle range by combining projection data collected in each of a plurality of third periods respectively close to the plurality of detected second periods of the projection data; and
reconstructing, using the computer, a second image of the organ based on projection data included in the data for reconstruction.

15. The imaging method according to claim 14, further comprising measuring, using the computer, feature quantities of regions corresponding to the organ to be imaged from the plurality of first images, wherein
the plurality of second periods are detected by the comparison of the feature quantities.

16. The imaging method according to claim 15, wherein
a low-speed fluctuation period during which a state where the variation of the feature quantities per unit time is smaller than a specified variation continues beyond a specified period is detected for each of the plurality of pulsation cycles, a plurality of pulsation phases which belong to pulsation cycles different from one another and in which the feature quantities are substantially the same is selected from among the pulsation phases included respectively in the plurality of detected low-speed fluctuation periods, and the plurality of third periods are detected as a plurality of periods different from one another respectively including the plurality of selected pulsation phases.

17. The imaging method according to claim 16, wherein the generating step, using the computer, includes:
selecting one of the projection directions regarding the projection data collected in the low-speed fluctuation period detected for the pulsation cycle is selected, for each of the plurality of pulsation cycles;
setting an angle range of a specified angle around the projection direction selected, for each of the plurality of pulsation cycles;
widening of the angle ranges set for the plurality of pulsation cycles until the required angle range is obtained by combining at least portions of the angle ranges of the plurality of pulsation cycles;
selecting at least partial ranges that cover the whole of the required angle range by combining the plurality of widened angle ranges, and that do not overlap one another for the plurality of pulsation cycles; and uses the selected at least partial ranges as available angle ranges
extracting projection data collected in the second periods from the projection data collected by the scanner, the second periods being the collection period of projection data in the projection direction in the available angle range selected for the same pulsation period in the slow-speed fluctuation period detected by the detecting for the pulsation cycle or at a timing closest to the low-speed fluctuation period for each of the plurality of pulsation cycles; and
generating the data for reconstruction as data including all of the extracted projection data.

18. The imaging method according to claim 17, wherein
when an overlap amount of two of the plurality of angle ranges having the increased angle is granter than a specified overlap amount, the projection direction is selected again to increase an angle between the two projection directions selected as a center of the two angle ranges, and then the setting of the angle ranges and the increase of the angle of the angle ranges are carried out, respectively.

19. The imaging method according to claim 17, wherein
an increasing speed of the angle range is increased all the more, as the low-speed fluctuation period detected for the pulsation cycle having the set angle range is longer.

* * * * *